United States Patent [19]

Marsico, Jr. et al.

[11] Patent Number: 4,610,981
[45] Date of Patent: Sep. 9, 1986

[54] N-[(1H-IMIDAZOL-1-YL) AND (1H-1,2,4-TRIAZOL-1-YL)-ALKYL]BENZENESULFONAMIDES AND THROMBOXANE SYNTHETASE/ANTIHYPERTENSIVE COMPOSITIONS

[75] Inventors: Joseph W. Marsico, Jr., Pearl River, N.Y.; William B. Wright, Jr., Woodcliff Lake, N.J.

[73] Assignee: American Cyanamid Company, Stamford, Conn.

[21] Appl. No.: 700,575

[22] Filed: Feb. 11, 1985

[51] Int. Cl.[4] ............... A61K 31/635; A61K 31/415; A61K 31/41; C07D 233/64
[52] U.S. Cl. ........................... 514/158; 514/383; 514/399; 546/338; 548/341; 548/262
[58] Field of Search ............... 546/338; 548/341, 262; 514/399, 158, 383, 357; 260/234.9

[56] References Cited

U.S. PATENT DOCUMENTS 3,629,332 12/1971 Harrington et al. ............... 546/338

OTHER PUBLICATIONS

Streitwieser, A., "Introduction to Organic Chemistry", (1976) p. 789.
Haines, P. G. et al., "Chemical Reactivity of Myosmine" J.A.C.S. 67 (1945) pp. 1258–1262.
Chemical Abstracts 55:P12425e (1959).

Primary Examiner—Henry R. Jiles
Assistant Examiner—Dale A. Bjorkman
Attorney, Agent, or Firm—Edward A. Conroy, Jr.

[57] ABSTRACT

This invention concerns novel N-[(1H-imidazol-1-yl), (1H-1,2,4-triazol-1-yl) and (3-pyridyl)alkyl]benzenesulfonamides which are useful as inhibitors of thromboxane synthetase enzyme and/or as antihypertensive agents.

21 Claims, No Drawings

N-[(1H-IMIDAZOL-1-YL) AND (1H-1,2,4-TRIAZOL-1-YL)-ALKYL]BENZENESULFONAMIDES AND THROMBOXANE SYNTHETASE/ANTIHYPERTENSIVE COMPOSITIONS

SUMMARY OF THE INVENTION

This invention relates to new organic compounds and, more particularly, is concerned with novel N-[(1H-imidazol-1-yl), (1H-1,2,4-triazol-1-yl) and (3-pyridyl)alkyl]benzenesulfonamides which may be represented by the following structural formula:

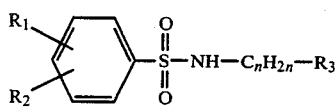

wherein $R_1$ and $R_2$ are individually selected from the group consisting of hydrogen, halogen, alkoxy($C_1$-$C_3$) and acylamino; $R_3$ is heteroaryl and is selected from the group consisting of imidazole, triazole and 3-pyridyl; and n is an integer from two to eight inclusive, together with the pharmaceutically acceptable salts thereof.

The novel compounds of the present invention are obtainable in general as colorless, white or pale yellow crystalline solids and in some cases may be oils. The solids have characteristic melting points and absorption spectra. The compounds are appreciably soluble in many organic solvents such as lower alkanols, chloroform, dichloromethane, tetrahydrofuran, acetone, N,N-dimethylformamide and the like, but are relatively insoluble in water.

The organic bases of the present invention form nontoxic acid-addition salts with a variety of pharmacologically acceptable organic and inorganic salt-forming reagents. Thus acid-addition salts, formed by admixture of the organic free base with one or more equivalents of an acid, suitably in a neutral solvent, are formed with such acids as sulfuric, phosphoric, hydrochloric, hydrobromic, sulfamic, citric, lactic, malic, succinic, maleic, fumaric, tartaric, acetic, benzoic, gluconic, ascorbic and the like. For purposes of this invention the free bases are equivalent to their nontoxic acid-addition salts. The acid-addition salts of the organic bases of this invention are difficult to obtain solid salts relatively soluble in water, methanol and ethanol but relatively insoluble in nonpolar organic solvents such as diethyl ether, benzene and toluene.

DETAILED DESCRIPTION OF THE INVENTION

The compounds of the present invention may be prepared according to the following reaction schemes, where $R_1$, $R_2$, $R_3$ and n are as described hereinabove:

METHOD I

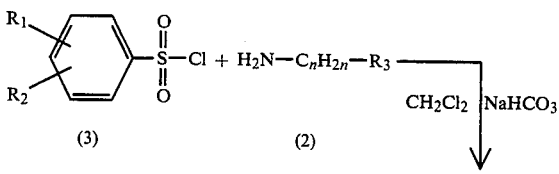

-continued
METHOD I

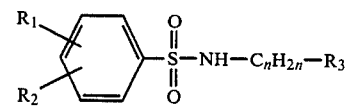

In accordance with Method I, an appropriate benzenesulfonyl chloride (3) is reacted with an 1H-imidazole-1-alkanamine, an 1H-1,2,4-triazole-1-alkanamine or a 3-pyridyl-alkanamine (2) either as the free base or a salt thereof, in an inert solvent such as dichloromethane and the like, containing an excess of saturated sodium bicarbonate solution for 8–48 hours, then isolated and the resulting product is purified by crystallization or chromatography. The final condensation of (2) and (3) is best carried out by adding (3) to the reaction mixture at ambient temperature and stirring vigorously.

METHOD II

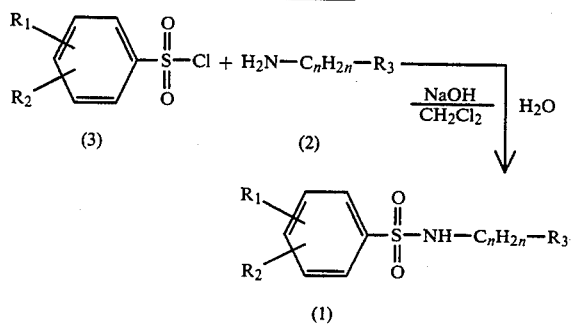

In accordance with Method II, an appropriate benzenesulfonyl chloride (3) is reacted with an 1H-imidazole-1-alkanamine, an 1H-1,2,4-triazole-1-alkanamine or a 3-pyridyl-alkanamine (2) by stirring in water or 1N sodium hydroxide for 16–24 hours. The addition of 5N aqueous base and a solvent such as dichloromethane or the like results in isolation of the desired product.

This invention also pertains to N-[(1H-imidazol-1-yl) and (1H-1,2,4-triazol-1-yl)alkyl]-1H-isoindole-1,3-(2H)-diones which may be represented by the following structural formula:

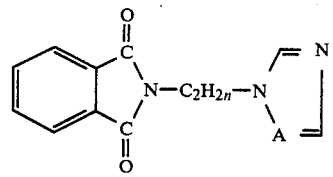

wherein n is an integer from two to eight, inclusive. These phthalimide derivatives are intermediates for the preparation of the hereinbefore described 1H-imidazole(and 1H-1,2,4-triazole)-1-alkanamines (2). The novel 1,3(2H)-dione intermediates (4) of the present invention may be readily prepared and used to prepare the 1H-imidazole(and 1H-1,2,4-triazole)-1-alkanamines (2) as set forth in the following reaction scheme (Method III) wherein n is as hereinbefore defined, A is nitrogen or —CH= and X is chloro or bromo.

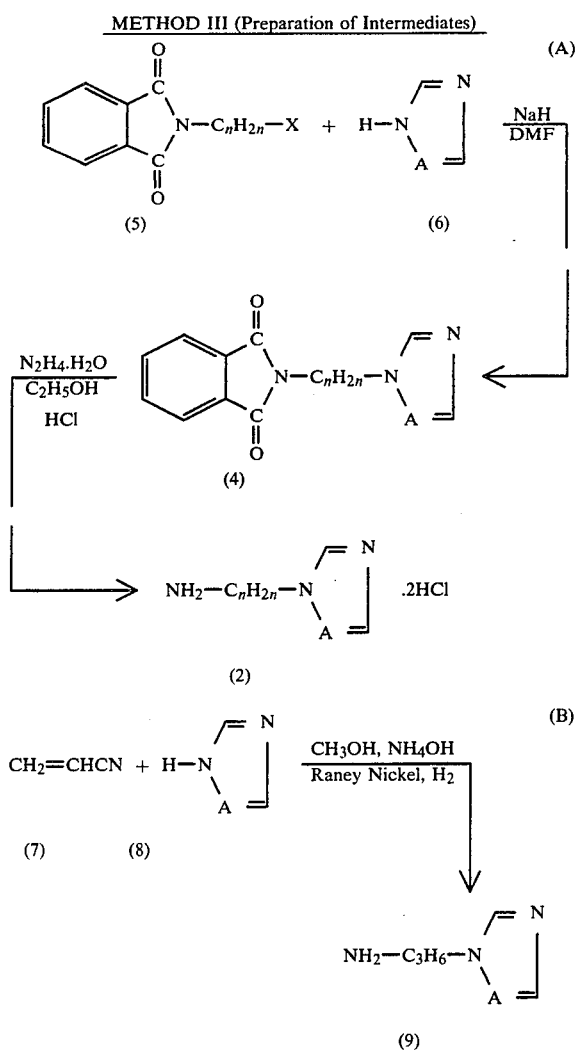

In accordance with Method IIIA, 1H-imidazole or 1H-1,2,4-triazole (6) is first converted to a salt form with silver nitrate, sodium hydride, and the like and then condensed with an appropriate N-haloalkylphthalimide (5) for about 4–8 hours, to obtain the corresponding 2-[(1H-imidazol-1-yl) or (1H-1,2,4-triazol-1-yl)alkyl]-1H-isoindole-1,3(2H)-dione intermediate (4), which is then reacted with hydrazine hydrate in ethanol at reflux for about 2–8 hours. Hydrochloric acid is then added and refluxing is continued for about 1–6 hours, giving the 1H-imidazole (or 1H-1,2,4-triazole)-1-alkanamine, dihydrochloride (2). The dihydrochloride (2) may be converted to the free base by treatment of an aqueous solution of the dihydrochloride with sodium or potassium hydroxide and extraction with a solvent such as chloroform or dichloromethane, then isolation from the organic phase.

In accordance with Method III B, acrylonitrile (7) and 1H-imidazole or 1H-1,2,4-triazole (8) are reacted with heat for about 2–4 hours, concentrated to an oil and then hydrogenated with Raney nickel catalyst in methanol and ammonium hydroxide for a period of about 8–10 hours, giving the 1H-imidazole(or 1H-1,2,4-triazole)-1-propanamine derivatives (9).

The compounds of this invention inhibit thromboxane synthetase enzyme without interfering with other enzymes in the arachadonic acid cascade. Thus, these compounds are useful in the treatment of diseases characterized by an imbalance of thromboxane $A_2$/prostacyclin such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects*, H. Barnett, P. Paoletti, E. Flamm and G. Brambilla, eds., Elsevier/North-Holland Biomedical Press, pp 137–150 (1981)]. Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthethase enzyme located in, for example, blood platelets. When $TXA_2$ production is increased relative to $PGI_2$, platelet aggregation, thrombosis and vasospasm may occur [*Lancet*, 1, 1216 (1977); *Lancet*, 1, 479 (1977); *Science*, 193, 1135 (1976); *Amer. J. Cardiology*, 41, 787 (1978)]. $TXA_2$ synthetase inhibitors have been shown to have superior anti-thrombotic action to that of aspirin [*J. Clin. Invest.*, 65, 400 (1980); *Br. J. Pharmac.*, 76, 3 (1982)].

The role of prostaglandins, including $TXA_2$ and $PGI_2$, in ischemic heart patients has been reviewed [*Cardiovascular Pharmacology of the Prostaglandins*, A. G. Herman, P. M. Vanhoute, H. Denolin and A. Goosens, eds., Raven Press, New York, pp 361–374 (1982)]. Injection of $TXA_2$ into coronary arteries of guinea pigs and rabbits causes myocardial ischemia and subendocardial necrosis [*Drugs of the Future*, 7, 331 (1982); Proc. Jap. Acad., 53(B), 38 (1977); *Eur. J. Pharmacol.*, 53 49 (1978)]. Recent research has demonstrated the beneficial effects of $PGI_2$ and selective inhibition of thromboxane synthetase on ischemic myocardium in canines [*J. Cardiovascular Pharmacology*, 4, 129 (1982)]. Thus, compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

The inhibition of thromboxane ($TXA_2$) formation was studied by determining the concentration of thromboxane $B_2$ ($TXB_2$), the stable hydrolysis product of $TXA_2$.

Under urethan anesthesia, 10 μl of arterial blood was collected in one ml of 3.2% sodium citrate in a polystyrene tube from Okamoto-Aoki spontaneously hypertensive rats (SHR) (Taconic Farms, Germantown, NY) between 19 and 24 weeks in age. The blood was diluted with 3 ml cold saline and centrifuged at room temperature for 15 minutes at 460×g. The platelet rich plasma (PRP) was separated. The platelets were isolated by centrifuging the PRP for 10 minutes at 1060×g and were washed in 4 ml cold oxygenated Krebs phosphate buffer, pH 7.4. The chilled platelets recovered from centrifuging at 800×g for 10 minutes were resuspended in oxygenated Krebs phosphate buffer and diluted to contain 4.5–6.0×$10^4$ platelets/μl.

Assay samples, prepared on ice, contained 200 μl platelet suspension, 50 μl saline, and 50 μl vehicle or drug under study. The samples were incubated for 10 minutes at 37° C. in a metabolic shaker. The reaction was terminated by immersing the tubes in an ice bath and adding 50 μl of 0.5M citric acid. The samples were centrifuged for 10 minutes in a refrigerated centrifuge and the supernatants thus obtained were decanted and stored at −20° C. The $TXB_2$ content for each sample was determined by a direct radioimmunoassay (RIA) utilizing a $TXB_2$ specific RIA kit purchased from New England Nuclear, Boston, MA and expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

| Compound | Dose (M) | % Inhibition |
|---|---|---|
| N—[4-(1H—Imidazol-1-yl)butyl]benzenesulfonamide | $10^{-4}$ | 93 |
| N—[3-(1H—1,2,4-Triazol-1-yl)propyl]benzenesulfonamide | $10^{-4}$ | 67 |
| 4-Chloro-N—[3-(1H—imidazol-1-yl)propyl]benzenesulfonamide | $10^{-4}$ | 99 |
| 4-Chloro-N—[4-(1H—imidazol-1-yl)butyl]benzenesulfonamide | $10^{-4}$ | 94 |
| 4-Bromo-N—[3-(1H—imidazol-1-yl)propyl]benzenesulfonamide | $10^{-4}$ | 100 |
| 4-Bromo-N—[4-(1H—imidazol-1-yl)butyl]benzenesulfonamide | $10^{-4}$ | 91 |
| N—[3-(1H—Imidazol-1-yl)propyl]-4-methoxybenzenesulfonamide | $10^{-4}$ | 100 |
| N—[4-(1H—Imidazol-1-yl)butyl]-4-methoxybenzenesulfonamide | $10^{-4}$ | 97 |
| N—[4-[[[3-(1H—Imidazol-1-yl)propyl]amino]sulfonyl]phenyl]acetamide | $10^{-4}$ | 73 |
| N—[4-[[[4-(1H—Imidazol-1-yl)butyl]amino]sulfonyl]phenyl]acetamide | $10^{-4}$ | 100 |
| 4-Chloro-N—[8-(1H—imidazol-1-yl)octyl]benzenesulfonamide | $10^{-4}$ | 93 |
| 4-Chloro-N—[5-(1H—imidazol-1-yl)pentyl]benzenesulfonamide hydrochloride | $10^{-4}$ | 97 |
| 4-Chloro-N—[2-(3-pyridyl)ethyl]benzenesulfonamide | $10^{-4}$ | 90 |

The novel compounds of the present invention also are active antihypertensive agents and were tested for hypotensive activity by the method of P. S. Chan and D. Poorvin, *Clinical and Experimental Hypertension*, 1(6), 817–830 (1979). Male, 16 week old, spontaneously hypertensive rats of the Okamoto strain, from Taconic Farms, Germantown, N.Y., having an average mean arterial blood pressure of 160±1.5 mm of mercury are used in the test. One to three rats are used per test compound. A rat is dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading, is given 24 hours later. At 28 hours after the initial dose the mean arterial blood pressure is measured by the method of Chan and Poorvin, vide supra. The procedure is repeated in a second and third rat when necessary.

The results of this test on representative compounds of the present invention appear in Table II below.

TABLE II

| Compound | MABP in mm Hg (no. of rats) |
|---|---|
| 4-Bromo-N—[2-(1H—imidazol-1-yl)ethyl]benzenesulfonamide | 125 (3) |
| 4-Chloro-N—[3-(1H—imidazol-1-yl)propyl]benzenesulfonamide | 120 (3) |
| 4-Chloro-N—[3-(1H—1,2,4-triazol-1-yl)propyl]benzenesulfonamide | 127 (3) |
| 4-Bromo-N—[3-(1H—imidazol-1-yl)propyl]benzenesulfonamide | 126 (4) |
| N—[4-(1H—Imidazol-1-yl)butyl]-4-methoxybenzenesulfonamide | 134 (3) |
| N—[4-[[[3-(1H—Imidazol-1-yl)propyl]amino]sulfonyl]phenyl]acetamide | 131 (2) |
| N—[4-[[[4-(1H—Imidazol-1-yl)butyl]amino]sulfonyl]phenyl]acetamide | 116 (3) |
| 4-Chloro-N—[8-(1H—imidazol-1-yl)octyl]benzenesulfonamide | 132 (3) |
| 4-Chloro-N—[5-(1H—imidazol-1-yl)pentyl]benzenesulfonamide | 119 (2) |
| 4-Chloro-N—[2-(3-pyridyl)ethyl]benzenesulfonamide | 109 (2) |

The novel compounds of the present invention have been found to be highly useful for inhibiting thromboxane synthetase and/or lowering elevated blood pressure in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 mg to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a matter of fact, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the finished composition. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be administered orally, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed.

The following specific examples illustrate the preparation of the compounds of the present invention and should not be construed to limit this invention in any way.

EXAMPLE 1

1H-Imidazole-1-propanamine

A mixture of 41 g of imidazole and 75 ml of acrylonitrile was heated on a steam bath for 3 hours, then concentrated under reduced pressure to remove excess acrylonitrile. A 300 ml portion of methanol was added to the residue together with 100 ml of concentrated ammonium hydroxide and 8 g of Raney nickel catalyst. This mixture was hydrogenated in a Parr apparatus until hydrogen uptake ceased and then filtered giving a light green liquid. A 300 ml portion of tetrahydrofuran was added to this liquid and the mixture filtered through diatomaceous earth. The filtrate was concentrated twice from toluene, giving 75.2 g of the desired intermediate as a clear oil. The dihydrochloride salt may be obtained by treating the base with ethanolic hydrochloric acid, concentrating and recrystallizating from ethanol.

EXAMPLE 2

2-[4-(1H-Imidazol-1-yl)butyl]-1H-isoindole-1,3(2H)-dione

A mixture of 0.2 mole of 2-(4-bromobutyl)-1H-isoindole-1,3(2H)-dione, 0.22 mole of sodium imidazole and 300 ml of dimethylformamide was stirred at 100° C. for 8 hours and then concentrated to remove the dimethylformamide. The residue was boiled with 500 ml of toluene and the insoluble material was removed by filtration. The toluene layer was concentrated to remove the solvent and the residue was further purified by HPLC using ethyl acetate and a PrepPAK®-500 silica gel column (Waters Associates, Millipore). The desired compound melted at 75°–77° C. Addition of ethanolic hydrogen chloride resulted in the hydrochloride salt, mp 200°–203° C.

EXAMPLE 3

2-[5-(1H-Imidazol-1-yl)pentyl]-1H-isoindole-1,3(2H)-dione hydrochloride

A mixture of 3.12 g of sodium imidazole, 8.88 g of N-(5-bromopentyl)phthalimide and 40 ml of N,N-dimethylformamide was heated in an oil bath at 100° C. for 9 hours and then concentrated to remove the solvent. Methylene chloride was added and the insoluble material was removed by filtration. The methylene chloride layer was washed twice with water, dried over magnesium sulfate and concentrated to an oil. An 11.0 ml amount of 2.74N ethanolic hydrogen chloride was added with ether to precipitate the hydrochloride salt as white crystals. The material was recrystallized twice from ethanol and gave the desired compound, mp 194°–197° C.

Using the same procedure, N-(8-bromooctyl)phthalimide was converted to 2-[8-(1H-imidazol-1-yl)octyl]-1H-isoindole-1,3(2H)-dione, mp 43°–45° C.

EXAMPLE 4

1H-Imidazole-1-butanamine

A mixture of 0.2 mole of 2-[4-(1H-imidazol-1-yl)butyl]-1H-isoindole-1,3(2H)-dione, 0.22 mole of hydrazine hydrate and 400 ml of ethanol was heated on a steam bath for 3 hours and then treated with 400 ml of 3N hydrochloric acid and heated at reflux for an additional 2 hours. The insoluble material was filtered off and the mother liquor was concentrated to a low volume and again filtered. The remainder of the volatile material was distilled off and the residue was treated with saturated potassium carbonate solution. The 1H-imidazole-1-butanamine was extracted into methylene chloride and further purified by distillation on a Kugelrohr apparatus. In a like manner from 2-[5-(1H-imidazol-1-yl)pentyl]-1H-isoindole-1,3(2H)-dione was prepared 1H-imidazole-1-pentanamine and from 2-[8-(1H-imidazol-1-yl)octyl]-1H-isoindole-1,3(2H)-dione was prepared 1H-imidazole-1-octanamine.

EXAMPLE 5

1H-1,2,4-Triazole-1-butanamine, dihydrochloride

A mixture of 9.0 g of 1H-1,2,4-triazole, 6.24 g of approximately 50% sodium hydride in oil and 130 ml of dimethylformamide was stirred for 1.5 hours, then 33 g of N-(4-bromobutyl)phthalimide was added and this mixture was heated on a steam bath for 6 hours, then concentrated to a solid residue. Water and methylene chloride were added, the organic layer was separated, washed with water, dried and concentrated to a residue. This residue was recrystallized from ethanol, giving 27.3 g of 2-[4-(1H-1,2,4-triazol-1-yl)butyl]-1H-isoindol-1,3(2H)-dione.

A mixture of 27 g of the above dione, 4.85 ml of hydrazine hydrate and 250 ml of ethanol was refluxed for 3 hours and then cooled. A 450 ml portion of 3N hydrochloric acid was added and the mixture was refluxed for about 3 hours, then concentrated to ½ volume and filtered. The filtrate was concentrated to a solid which was reconcentrated twice from ethanol, giving 18.2 g of the desired intermediate as white crystals, mp 183°–186° C.

EXAMPLE 6

1H-1,2,4-Triazole-1-propanamine

A mixture of 20.7 g of 1H-1,2,4-triazole and 37.5 ml of acrylonitrile was heated on a steam bath for 3 hours and then concentrated to an oil. This oil was added to 200 ml of methanol and 100 ml of concentrated ammonium hydroxide containing Raney nickel catalyst in a Parr apparatus and hydrogenated for 8 hours with an uptake of about 46 psi of hydrogen. The catalyst was removed by filtration and ethanol was added to the filtrate. The mixture was filtered, the filtrate was concentrated, then reconcentrated from toluene, giving 36.6 g of the desired intermediate as an oil.

EXAMPLE 7

1H-1,2,4-Triazole-1-pentanamine

A mixture of 5.92 g of N-(5-bromopentyl)phthalimide, 2.07 g of sodium triazole and 25 ml of dimethylformamide was heated in an oil bath at 100° C. for 9 hours and then concentrated to remove the solvent. Methylene chloride was added and the insoluble material removed by filtration. The methylene chloride layer was washed with water, dried and concentrated. The residue was treated with ethanolic hydrochloric acid and ether and the crystalline material recovered by filtration. On recrystallization from ethanol, 2-[5-(1H-1,2,4-triazole-1-yl)pentyl]-1H-isoindol-1,3(2H)-dione, hydrochloride, mp 185°–188° C. was obtained.

A mixture of 7.4 g of the above dione, 2.2 g of sodium carbonate and 10 ml of water was stirred and methylene chloride was added. The layers were separated and the organic layer dried and concentrated to remove the solvent. The residual oil, 1.0 ml of hydrazine hydrate and 80 ml of ethanol were refluxed for about 3 hours, cooled and 100 ml of approximately 3N hydrochloric acid was added. This mixture was refluxed for 2 hours, concentrated, water was added and the mixture was filtered. The filtrate was concentrated to remove volatile material and the crude dihydrochloride salt was treated with saturated potassium carbonate solution and extracted with methylene chloride. The organic layer was dried over magnesium sulfate and concentrated to obtain the desired compound as an oil.

EXAMPLE 8

N-[4-(1H-Imidazol-1-yl)butyl]benzenesulfonamide

To a stirred mixture of 1.39 g of 1H-imidazole-1-butanamine in 30 ml of dichloromethane containing an excess of saturated sodium bicarbonate solution was added, all at once at room temperature, a solution of 1.27 ml (1.76 g) of benzenesulfonyl chloride in 15 ml of dichloromethane. The mixture was stirred at room temperature for 22 hours. The layers were separated and the organic phase was dried over magnesium sulfate, then evaporated in vacuo to give an oil which crystallized on standing. The material was recrystallized from 20 ml of diethyl ether to give 1.40 g of colorless crystals, mp 119°–122° C.

Following the general procedure of Example 8 and reacting the appropriate benzenesulfonyl chloride with 1H-imdazol-1-propanamine or 1H-imidazol-1-butanamine in the presence of saturated sodium bicarbonate in dichloromethane for 16–48 hours, then crystallizing the respective products with ether and, if necessary, recrystallization from ethyl acetate or ethanol/dichloromethane gave the compounds of Examples 9–12 found in Table III below and gives the compounds of Examples 13–15 in Table III.

TABLE III

| Ex. | Benzenesulfonyl Chloride | Compound | MP °C. |
|---|---|---|---|
| 9 | 4-Chlorobenzenesulfonyl chloride | 4-Chloro-N—[3-(1H—imidazol-1-yl)propyl]benzenesulfonamide | 104–108 |
| 10 | 4-Methoxybenzenesulfonyl chloride | N—[3-(1H—Imidazol-1-yl)propyl]-4-methoxybenzenesulfonamide | 95–97 |
| 11 | 4-Chlorobenzenesulfonyl chloride | 4-Chloro-N—[4-(1H—imidazol-1-yl)butyl]benzenesulfonamide | 153–158 |
| 12 | 4-Methoxybenzenesulfonyl chloride | N—[4-(1H—imidazol-1-yl)butyl]-4-methoxybenzenesulfonamide | 123–127 |
| 13 | 2-Chlorobenzenesulfonyl chloride | 2-Chloro-N—[3-(1H—imidazol-1-yl)propyl]benzenesulfonamide | |
| 14 | 3-Bromobenzenesulfonyl chloride | 4-Bromo-N—[3-(1H—imidazol-1-yl)propyl]benzenesulfonamide | |
| 15 | 3,4-Dichlorobenzenesulfonyl chloride | 3,4-Dichloro-N—[3-(1H—imidazol-1-yl)propyl]benzenesulfonamide | |

EXAMPLE 16

N-[3-(1H-1,2,4-Triazol-1-yl)propyl]benzenesulfonamide

To a stirred mixture of 1.26 g of 1H-1,2,4-triazole-1-propanamine in 30 ml of dichloromethane containing an excess of saturated sodium bicarbonate solution was added, all at once at room temperature, a solution of 1.27 ml of benzenesulfonyl chloride in 15 ml of dichloromethane. The mixture was stirred at room temperature for 16 hours. The layers were separated. The dichloromethane layer was evaporated in vacuo and gave the compound of the Example as a colorless oil.

EXAMPLE 17

N-[4-[[[3-(1H-Imidazol-1-yl)propyl]amino]sulfonyl]phenyl]acetamide

A mixture of 1.25 g of 1H-imidazol-1-propanamine in 25 ml of water was stirred at room temperature then 2.34 g of N-acetylsulfanilyl chloride was added and stirring was continued for 20 hours resulting in a clear solution. With the addition of 4 ml of 5N sodium hydroxide the solution turned milky and resulted in the separation of an oil. The addition of dichloromethane resulted in the formation of a suspended precipitate which was collected by filtration and gave 2.67 g of the desired compound as tan crystals, mp 178°–180° C.

Following the general procedure of Example 17, and reacting the appropriate benzenesulfonyl chloride with 1H-imidazol-1-propanamine or 1H-imidazol-1-butanamine in the presence of aqueous sodium hydroxide and dichloromethane, gave the compounds of Examples 18-19 found in Table IV below.

TABLE IV

| Ex. | Benzenesulfonyl Chloride | Compound | MP °C. |
|---|---|---|---|
| 18 | N—Acetylsulfanilyl chloride | N—[4-[[[4-(1H—imidazol-1-yl)butyl]amino]sulfonyl]phenyl]acetamide | 165–168 |
| 19 | 4-Bromobenzenesulfonyl chloride | 4-Bromo-N—[3-(1H—imidazol-1-yl)propyl]benzenesulfonamide | 124–128 |

EXAMPLE 20

4-Bromo-N-[4-(1H-imidazol-1-yl)butyl]benzenesulfonamide

To a stirred solution of 1.39 g of 1H-imidazole-1-butanamine in 50 ml of dichloromethane at room temperature, covered with an excess of saturated sodium bicarbonate solution was added 2.55 g of 4-bromobenzenesulfonyl chloride. Stirring was continued for 22 hours, then the layers were separated and the organic layer was dried over magnesium sulfate and evaporated in vacuo. The residue was recrystallized from ethanol. The recrystallized material was dissolved in dichloromethane containing 5% ethanol. The solution was passed through a silica gel column. The column was washed twice with 200 ml portions of ethyl acetate, then three times with 200 ml portions of 10% ethanol/ethyl acetate. The 10% ethanol/ethyl acetate cuts were combined and evaporated in vacuo, the residue was dried in vacuo at 50° C. and gave 1.09 g of the compound of the Example as colorless crystals, mp 158°–159° C.

EXAMPLE 21

4-Chloro-N-[5-(1H-imidazol-1-yl)pentyl]benzenesulfonamide hydrochloride

The compound of this Example, mp 157°–161° C., was obtained when 1H-imidazole-1-pentanamine was reacted with 4-chlorobenzenesulfonyl chloride by the procedure of Example 20.

EXAMPLE 22

4-Bromo-N-[2-(1H-imidazol-1-yl)ethyl]benzenesulfonamide

When 1H-imidazole-1-ethanamine was treated with 4-bromobenzenesulfonyl chloride by the procedure of Example 20, the compound of this example, mp 165°–167° C., was obtained.

EXAMPLE 23

4-Chloro-N-[8-(1H-imidazol-1-yl)octyl]benzenesulfonamide

The compound of this Example, mp 54°–56° C., was obtained when 4-chlorobenzenesulfonyl chloride was reacted with 1H-imidazole-1-octanamine by the procedure of Example 20.

EXAMPLE 24

4-Chloro-N-[3-(1H-1,2,4-triazol-1-yl)propyl]benzenesulfonamide

To a stirred mixture of 1.89 g of 1H-1,2,4-triazole-1-propanamine in 50 ml of dichloromethane containing an excess of saturated sodium bicarbonate solution was added, all at once, 3.17 g of 4-chlorobenzenesulfonyl chloride. Vigorous stirring was continued for 24 hours. The layers were separated and the organic layer was dried over anhydrous magnesium sulfate, filtered and evaporated in vacuo to give a gum.

A small portion of gum was placed on a watch glass and scratched intermittently until crystallization occurred. The gum was covered with diethyl ether and seeded to initiate crystallization. The crystallized material was collected by filtration, washed with ether and air dried and gave 3.54 g of the desired compound as colorless crystals, mp 77°–79° C.

EXAMPLE 25

4-Chloro-N-[2-(3-pyridyl)ethyl]benzenesulfonamide

A mixture of 2.44 g of 2-(3-pyridyl)ethylamine (prepared according to Walker and Benson, *J. Am. Chem. Soc.*, 102, 5532 (1980)) and 25 ml of water was stirred and 4.22 g of 4-chlorobenzenesulfonyl chloride was aded. The mixture was stirred for 18 hours and then methylene chloride, water and 4 ml of 5N sodium hydroxide were added. The layers were separated and the organic layer was washed with water, dried over magnesium sulfate and concentrated. The residue was triturated with ether and the orange crystals which separated were removed by filtration and gave the compound of the Example, mp 143°–145° C.

We claim:

1. A compound selected from the group consisting of those of the formula:

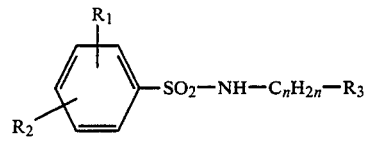

wherein $R_1$ and $R_2$ are the same or different and are each hydrogen, halogen, alkoxy ($C_1$–$C_3$) or acetylamino, $R_3$ is 1H-imidazol-1-yl or 1H-1,2,4-triazol-1-yl, and n is an integer from 2 to 8 inclusive; and the pharmacologically acceptable acid-addition salts thereof.

2. The compound according to claim 1; N-[4-(1H-imidazol-1-yl)butyl]benzenesulfonamide.

3. The compound according to claim 1; N-[3-(1H-1,2,4-triazol-1-yl)propyl]benzenesulfonamide.

4. The compound according to claim 1; 4-chloro-N-[3-(1H-imidazol-1-yl)propyl]benzenesulfonamide.

5. The compound according to claim 1; 4-chloro-N-[3-(1H-1,2,4-triazol-1-yl)propyl]benzenensulfonamide.

6. The compound according to claim 1; 4-chloro-N-[4-(1H-imidazol-1-yl)butyl]benzenesulfonamide.

7. The compound according to claim 1; 4-bromo-N-[3-(1H-imidazol-1-yl)propyl]benzenesulfonamide.

8. The compound according to claim 1; 4-bromo-N-[4-(1H-imidazol-1-yl)butyl]benzenesulfonamide.

9. The compound according to claim 1; 4-methoxy-N-[3-(1H-imidazol-1-yl)propyl]benzenesulfonamide.

10. The compound according to claim 1; 4-methoxy-N-[4-(1H-imidazol-1-yl)butyl]benzenesulfonamide.

11. The compound according to claim 1; N-[4-[[[3-(1H-imidazol-1-yl)propyl]amino]sulfonyl]phenyl]acetamide.

12. The compound according to claim 1; N-[4-[[[4-(H-imidazol-1-yl)butyl]amino]sulfonyl]phenyl]acetamide.

13. The compound according to claim 1; 4-chloro-N-[8-(1H-imidazol-1-yl)octyl]benzenesulfonamide.

14. The compound according to claim 1; 4-bromo-N-[2-(1H-imidazol-1-yl)ethyl]benzenesulfonamide.

15. The compound according to claim 1; 4-chloro-N-[5-(1H-imidazol-1-yl)pentyl]benzenesulfonamide hydrochloride.

16. A method of inhibiting thromboxane synthetase enzyme in a mammal which comprises administering internally to said mammal a thromboxane synthetase enzyme inhibiting amount of a compound of claim 1.

17. A thromboxane synthetase enzyme inhibiting composition of matter in dosage unit form which comprises an amount of a compound of claim 1 effective therefore in association with a pharmaceutically acceptable carrier.

18. A thromboxane synthetase enzyme inhibiting composition of water as recited in claim 17 wherein the dosage unit comprises from about 10 mg. to about 700 mg. of the compound in association with the pharmaceutically acceptable carrier.

19. A method of lowering elevated blood pressure in mammal which comprises administering internally to said mammal an effective amount of a compound of claim 1.

20. A therapeutic composition of matter in dosage unit form useful for lower elevated blood pressure in mammals which comprises an amount of a compound of claim 1 effective therefore in association with a pharmaceutically acceptable carrier.

21. A therapeutic composition of matter as recited in claim 20 wherein the dosage unit comprises from about 10 mg. to about 700 mg. of the compound in association with the pharmaceutically acceptable carrier.

* * * * *